United States Patent
Al-Mohizea

(10) Patent No.: US 8,936,557 B2
(45) Date of Patent: Jan. 20, 2015

(54) PUNCH BIOPSY DEVICE

(75) Inventor: Saad I. Al-Mohizea, Riyadh (SA)

(73) Assignee: King Saud University, Riyadh (SA)

( * ) Notice: Subject to any disclaimer, the term of this patent is extended or adjusted under 35 U.S.C. 154(b) by 1200 days.

(21) Appl. No.: 12/559,008

(22) Filed: Sep. 14, 2009

(65) Prior Publication Data

US 2010/0185116 A1   Jul. 22, 2010

(30) Foreign Application Priority Data

Jan. 19, 2009   (SA) ................... 109300037

(51) Int. Cl.
| | | |
|---|---|---|
| A61B 10/02 | (2006.01) | |
| A61B 17/32 | (2006.01) | |
| A61B 17/00 | (2006.01) | |

(52) U.S. Cl.
CPC ......... *A61B 10/0233* (2013.01); *A61B 10/0266* (2013.01); *A61B 2017/00752* (2013.01)
USPC .......................................... 600/567; 606/184

(58) Field of Classification Search
USPC .......... 600/564, 562, 565–568; 606/167, 170, 606/184
See application file for complete search history.

(56) References Cited

U.S. PATENT DOCUMENTS

| | | | |
|---|---|---|---|
| 3,512,519 A * | 5/1970 | Hall .............................. | 600/567 |
| 3,577,979 A | 5/1971 | van der Gaast | |
| 5,148,813 A | 9/1992 | Bucalo | |
| 5,848,978 A | 12/1998 | Cecchi | |
| 6,083,237 A | 7/2000 | Huitema et al. | |
| 6,764,495 B2 | 7/2004 | Lee et al. | |
| 6,792,305 B2 * | 9/2004 | Rastorgoueff et al. ........ | 600/564 |
| 7,819,888 B2 * | 10/2010 | Johanson et al. ............. | 600/567 |
| 2007/0232954 A1 | 10/2007 | Harris et al. | |
| 2007/0249960 A1 | 10/2007 | Williamson | |
| 2008/0300507 A1 * | 12/2008 | Figueredo et al. ............ | 600/567 |
| 2009/0018467 A1 | 1/2009 | Chiu et al. | |

FOREIGN PATENT DOCUMENTS

WO   WO-2006121619 A2   11/2006

* cited by examiner

*Primary Examiner* — Lee S Cohen
*Assistant Examiner* — Emily Lloyd
(74) *Attorney, Agent, or Firm* — Hart IP Law & Strategies

(57) ABSTRACT

A punch biopsy device is disclosed with an integrated tissue base cutting component. In an embodiment, the punch biopsy device includes a cutting blade with first and second arms operatively coupled to a handle. The punch biopsy device includes a prong flexible and integral to the cutting blade, the prong comprising top and lateral sharp edges configured to pierce and cut tissue, respectively. The prong is configured to be inserted into a body in a neutral position with the prong parallel with the first and second arms. The prong is configured to move to a position perpendicular to the first and second arms when the cutting blade is withdrawn to allow for the prong to catch and pierce the tissue. The prong is configured to cut the tissue while in the position perpendicular to the first and second arms when the cutting blade is rotated manually via the handle.

5 Claims, 13 Drawing Sheets

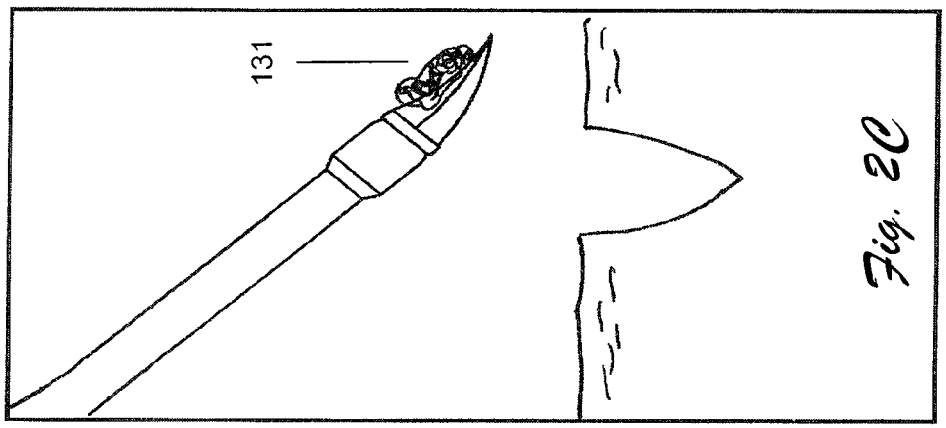
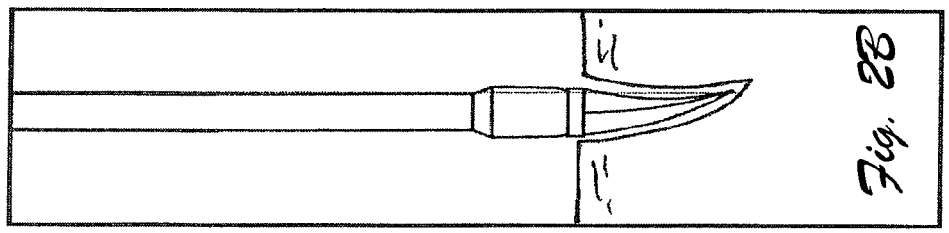
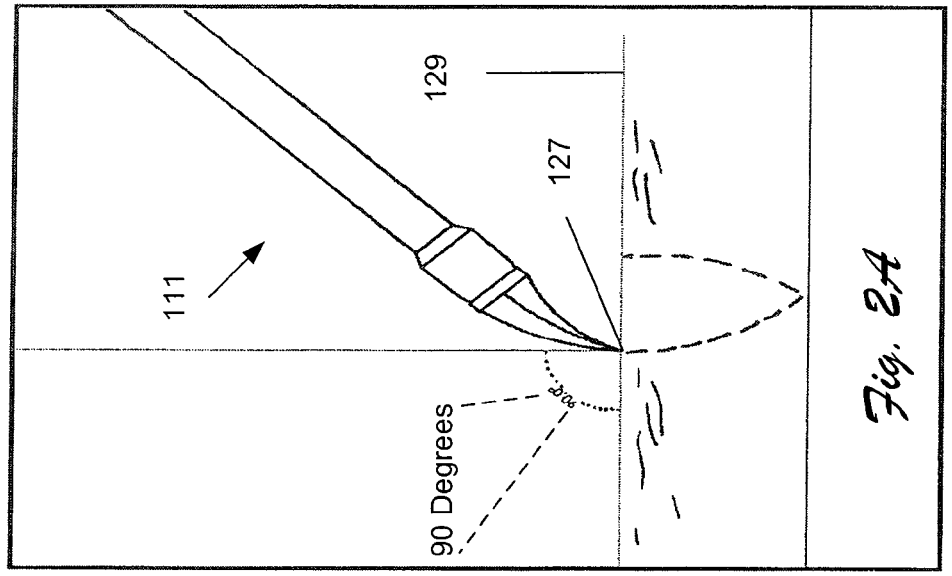

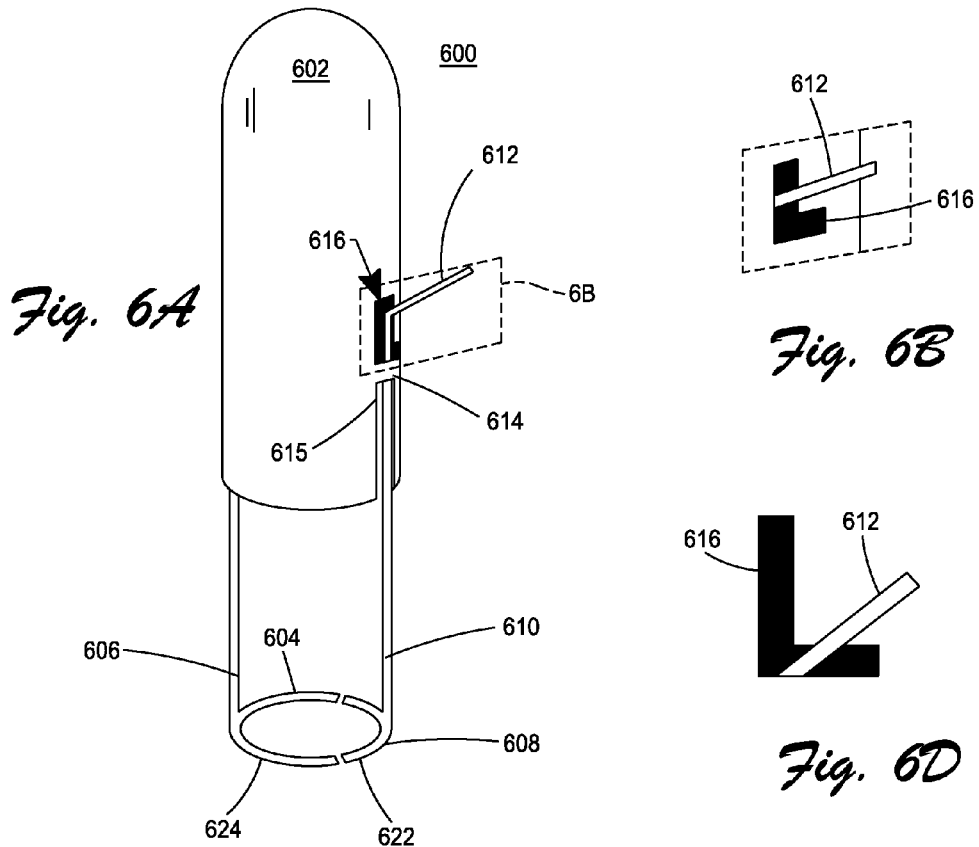
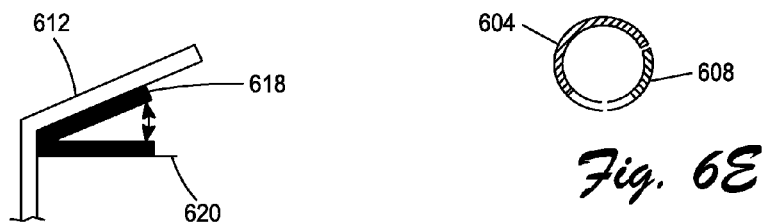

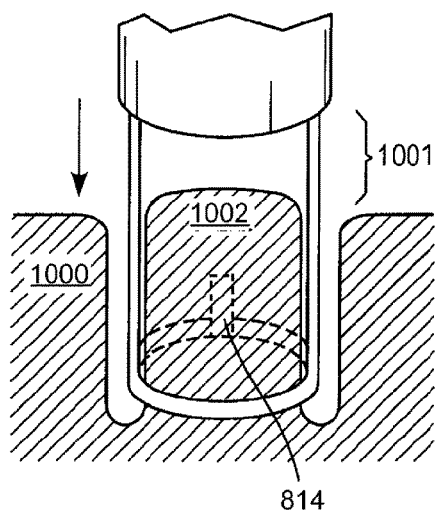
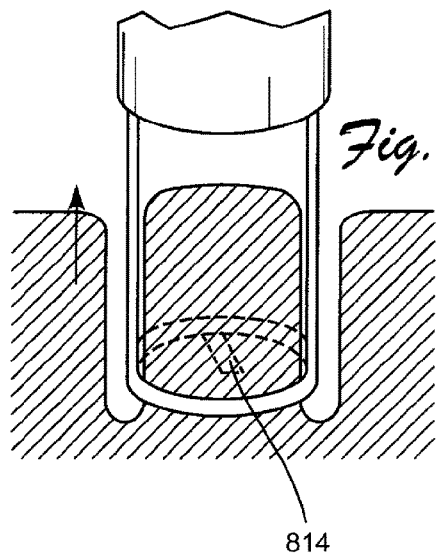
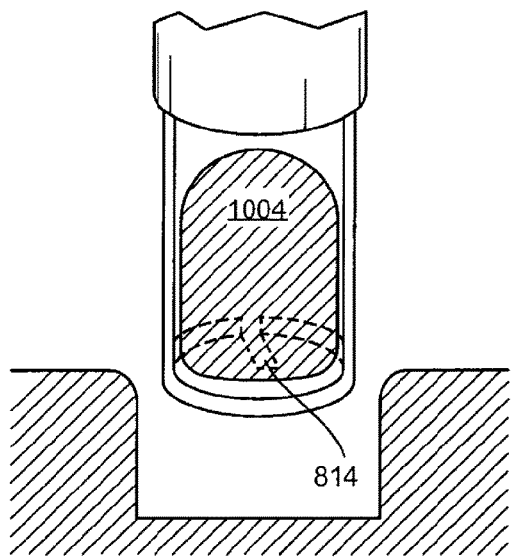

PUNCH BIOPSY DEVICE

RELATED APPLICATIONS

This patent application claims priority under 35 USC §119 to Saudi Arabian Patent Application Serial No. 109300037, which was filed on Jan. 19, 2009.

BACKGROUND

A punch biopsy is a common diagnostic procedure used for excision or procuring a tissue specimen for histopathological examination. Although any organ can be biopsied, biopsy punches are commonly used to take patient (human and animal patients) biopsies of skin and hair. Punch biopsies are usually done with a simple biopsy punch that includes two members: a handle and a cutting member made of steel. The cutting member is generally a hollow cylinder that is sharp at a lower edge. The punch biopsy procedure is initiated by pressing and rotating the biopsy punch against tissue at a desired location for the biopsy. The biopsy punch then is pulled back and a needle or tweezers are used to stabilize tissue cut by the biopsy punch. The stabilized tissue then is cut at a base of the tissue with scissors or a blade.

Although the biopsy punch is relatively easy to make and the punch biopsy procedure is relatively easy to perform, there are negative aspects of the biopsy punch and associated tissue cutting procedure. For example, needles typically are used in the biopsy punch cutting procedure to expose and stabilize the base of the tissue prior to cutting with the scissors or blade, or to dislodge a biopsied specimen from a chamber of the biopsy punch. In such scenarios, doctors are susceptible to accidentally sticking themselves or an assistant with the needle. Additionally, use of tweezers also can cause problems. For example, holding the tissue too firmly with the tweezers can compromise the usefulness of the tissue for histopathology by creating artifacts that may confuse histopathology results. Other problems with punch biopsy procedures may include inadequate sample removal. Due to bleeding and fear of pulling on tissue, a practitioner may cut the tissue too shallow. Shallow cuts produce insufficient biopsies due to part or all of the subcutaneous tissue being left on the patient (i.e., the entity/target undergoing treatment—may be a person or animal).

Punch biopsy procedures have also been used to harvest hair grafts for hair transplantation in a process called follicular unit extraction. The standard biopsy punches are less than ideal for hair transplantation. Hair transplantation requires that the hair bulge and bulb, which are located deeper than the upper epidermal layers, be removed. Standard biopsy punches, however, do not penetrate deeply enough to adequately remove the hair bulge and bulb. In ideal hair transplantation, the upper layers of tissue are left behind to minimize scarring while more tissue is taken below the skin surface. U.S. Pat. No. 3,577,979 attempts to address these problems by using a set of short prongs located inside a cutting member to pierce skin if a biopsy punch is rotated in a direction opposite the direction of the prongs. The short prongs, however, may damage a tissue specimen and do not provide a component to cut the base of the tissue. The short prongs stabilize the tissue for cutting by scissors. U.S. Patent Application Publication No. 2007/0232954 generates elliptical biopsies by oscillating two cutter blades which are curved sideways and flat from top to bottom using a motor drive. The device, however, produces only superficial biopsies, up to 4 mm deep, which leaves part of the dermis and subcutaneous tissue behind. Furthermore, due to the curved shape of the blades, the blades may fail to completely cut the tissue.

SUMMARY

Systems and methods for a scoop blade biopsy device are described. In one aspect, a biopsy device has a scoop-shaped blade with a distal pointed tip. A handle is coupled to a proximal end of the scoop-shaped blade. The scoop-shaped blade and handle combination of the biopsy device are configured and responsive to a manually directed biopsy operation on a patient.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIGS. 2A-2C show an exemplary sequence of operations for a scoop-shaped blade biopsy device, according to one embodiment.

FIG. 6A shows an exemplary punch biopsy device with a semicircle cutting blade and a corresponding tissue stabilizing assembly to facilitate cutting the base of a cored tissue sample, according to one embodiment.

FIG. 6B shows an exemplary implementation of a key gap in a punch biopsy device to allow for movement of a tissue stabilizing arc via an actuating lever operatively coupled to the end of the tissue stabilizing arc, according to one embodiment.

FIG. 6C shows an exemplary spring configuration to snap a stabilizing arm in a punch biopsy device to a substantially neutral position with respect to a tissue sample in a tissue retaining portion of the biopsy device, according to one embodiment.

FIG. 6D shows an exemplary configuration of biopsy tissue stabilizing arm actuating key in a locked position in a key gap, according to one embodiment.

FIG. 6E is an exemplary illustration showing the position of gaps between a cutting blade and a tissue stabilizing arc in a punch biopsy device, according to one embodiment.

FIGS. 10A-10C show various aspects of an exemplary punch biopsy device with a tissue sample base cutting prong, according to one embodiment.

DETAILED DESCRIPTION

An Exemplary Scoop-Shaped Blade Biopsy Device

Figure 1:
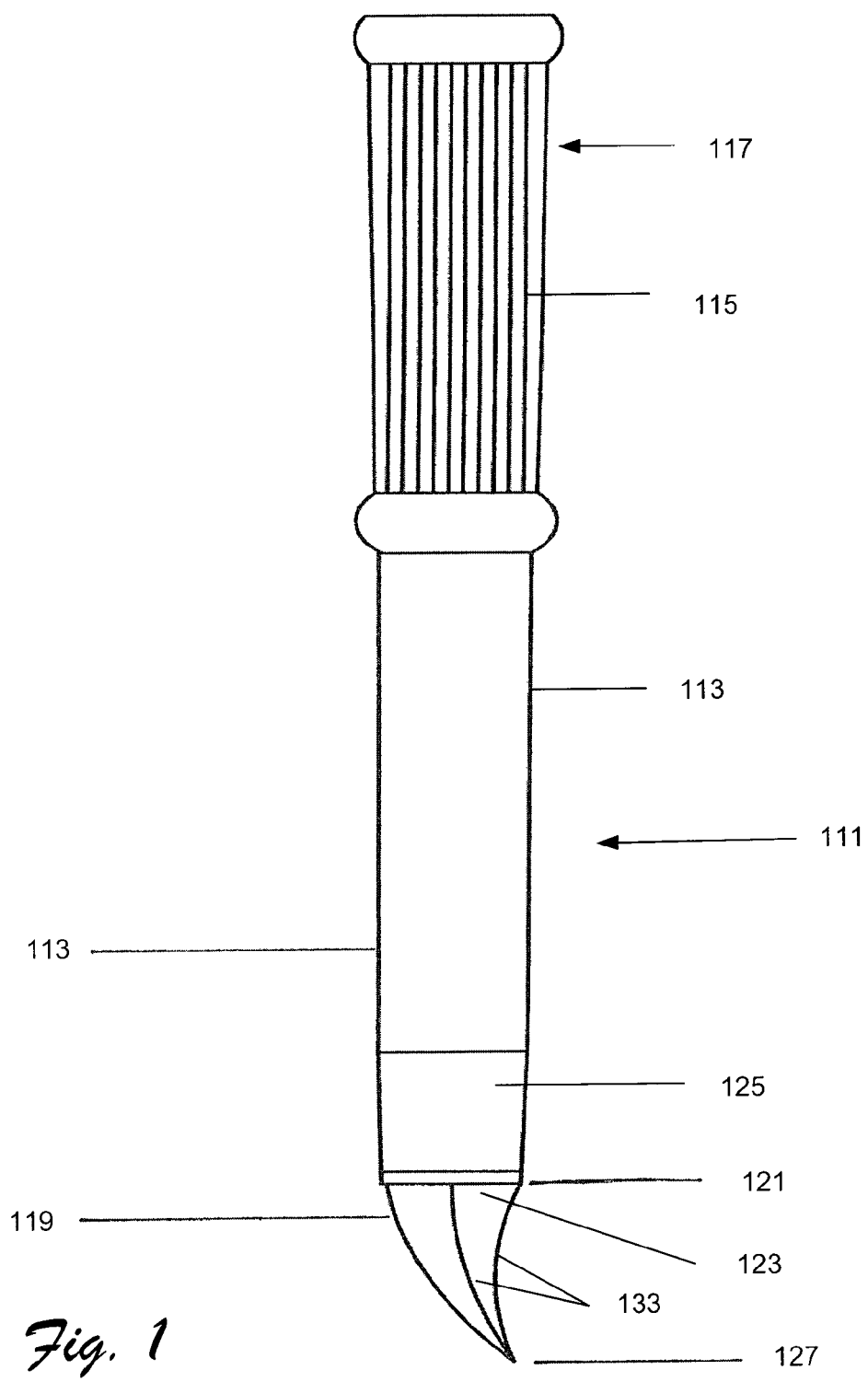
FIG. 1 shows an exemplary scoop-shaped blade biopsy device, according to one embodiment.

FIG. 1 shows a scoop-shaped blade biopsy device 111, according to one embodiment. The scoop-shaped blade device 111 is not a punch biopsy device. In this implementation, the scoop-shaped blade biopsy device 111 includes a handle 113. In various embodiments, the handle 113 is hollow or solid. In certain embodiments, the handle 113 includes grip improvement mechanisms 115 such as ridges, serrations, or dimples, or rubber or other non-skid materials. In various embodiments, the grip improvement mechanisms 115 may be located at a proximal end 117 of the handle 113 or may cover the entire handle 113. The handle 113 may be made of plastic, stainless steel, or other suitable materials.

In the embodiment of FIG. 1, a cutting member 119 is coupled to the handle 113 at a connector 121. A proximal end 123 of the cutting member 119 may be coupled to a distal end 125 of the handle 113 at the connector 121. The cutting member 119 may be a scoop-shaped blade with a pointed tip 127. In certain embodiments, the cutting member 119 has a scoop-shaped blade that forms a triangular arc. The cutting member 119 may be made of stainless steel or other suitable materials that are hard and have edges that are sharp or may be sharpened. In the embodiment of FIG. 1, cutting edges 133 of the cutting member 119, when viewed from a side, form a quarter of a lens or ellipse. In certain embodiments, the cutting member is sharp on all edges 133 except the edge coupled to the handle 113, which allows the cutting member 119 to cut both downwards and sideways. The cutting member 119 may be curved both from side to side and axially from the proximal end 123 to the pointed tip 127. In certain embodiments, a side-to-side curvature dictates a diameter of the tissue biopsy, and an axial curvature determines a depth of the tissue biopsy.

FIGS. 2A-2C show an exemplary sequence of operation for a scoop-shaped blade biopsy device, according to one embodiment. Referring to FIG. 2A, the pointed tip 127 of the biopsy device 111 is held at an angle relative to a tissue surface 129. In certain embodiments, the angle relative to the tissue surface 129 may be 90 degrees, but other angles may be used. The tissue surface may then be punctured with the pointed tip 127. After puncturing the skin, the biopsy device 111 is pushed forward and downward in an arc-like direction until the entire cutting member 119 is embedded within the tissue, as shown in FIG. 2B. The scooped shape of the cutting member 119 facilitates direction of the cutting member 119 into an appropriate location. In certain embodiments, the biopsy device 111 is rotated around its longitudinal axis, which is approximately perpendicular to the tissue surface 129, to completely sever a tissue biopsy 131. In certain embodiments, if necessary, the biopsy device 111 may be tilted away from the approximately perpendicular orientation relative to the tissue surface 129 to completely sever the tissue biopsy 131. Referring to FIG. 2C, the biopsy device 111 is lifted away from the tissue surface 129 with the tissue biopsy 131. The tissue biopsy 131 may be removed from the biopsy device 111, for example, by shaking the biopsy device 111.

In the embodiments of FIGS. 2A-2C, the shape of the tissue biopsy 131 is a half lens or half ellipse cut across the short axis. The depth of the tissue biopsy 131 may depend on the angle of penetration and the axial curvature of the cutting member 119 of the biopsy device 111. In certain embodiments, an angle of approximately 90 degrees is preferred, as other angles may fail to completely sever the tissue biopsy 131 from a patient or may produce a superficial biopsy.

Figure 3A:
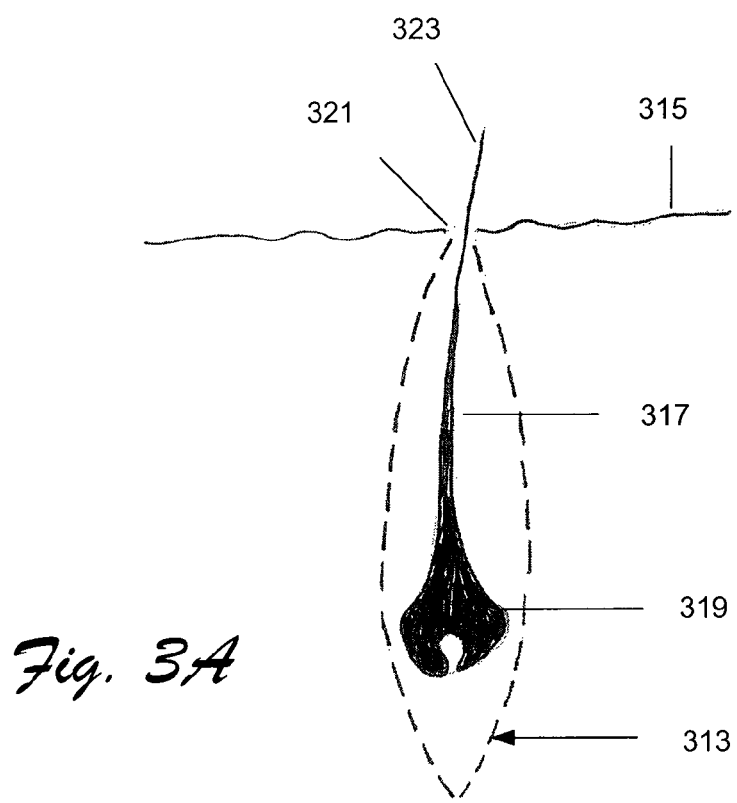
FIG. 3A is an exemplary cross-sectional view of a path of a scoop-shaped blade biopsy device used in hair harvesting, according to one embodiment.
Figure 3B:
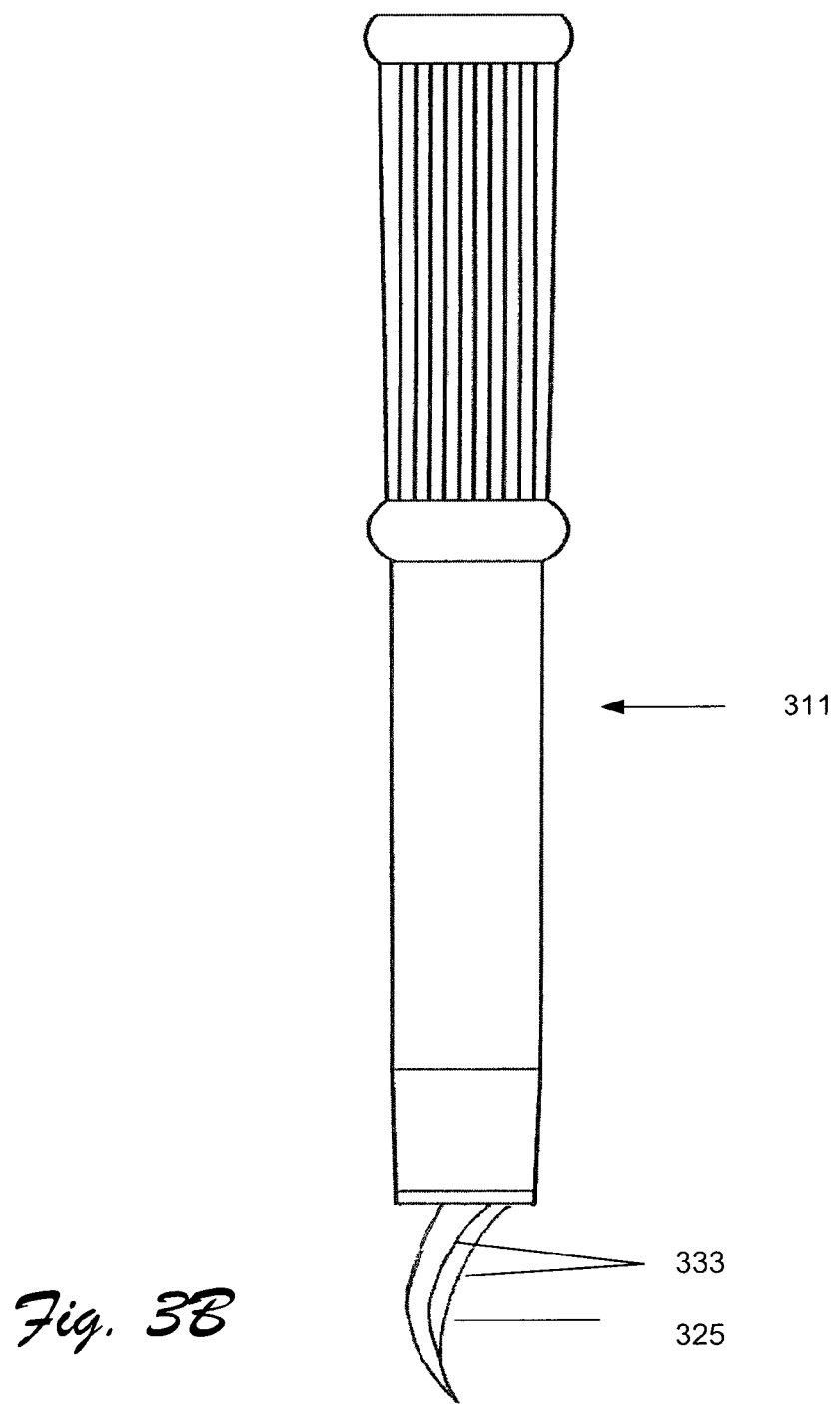
FIG. 3B shows an exemplary scoop-shaped blade biopsy device used in hair harvesting, according to one embodiment.
Figure 3C:
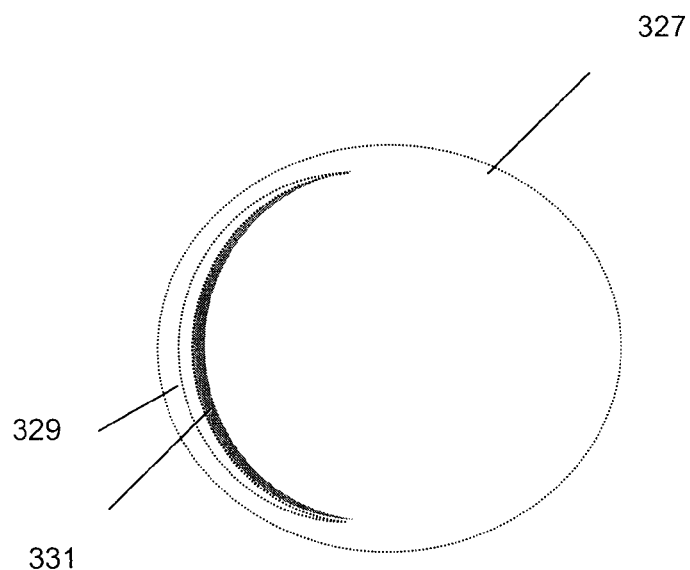
FIG. 3C is an exemplary top plan view of a base used with a scoop-shaped blade biopsy device, according to one embodiment.

FIGS. 3A-3C show a scoop-shaped blade biopsy device 311, according to one embodiment. The biopsy device 311, for example, may be used in hair transplantation, and more specifically for follicular unit extraction. Referring to FIG. 3A, a lens or elliptical biopsy 313, relative to the vertical axis, is produced by a scoop-shaped blade biopsy device 311, as shown in FIG. 3B. In certain embodiments, the lens or elliptical biopsy 313 minimizes scarring in situations where the epidermis 315 is not crucial and deeper structures such as a hair bulge 317 and bulb 319 are harvested. The lens or elliptical biopsy 313 may be produced when a penetration angle is less than approximately 90 degrees, such as approximately 40 degrees to approximately 70 degrees. In certain embodiments, an entry point 321 is at an emergence of a hair shaft 323.

Referring to FIG. 3B, edges 333 of a cutting member 325 form a half lens or half ellipse viewed from the side. By choosing an appropriate angle of entry for the cutting member 325, which depends on the direction of the hair shaft 323 and the curvature of the cutting member 325, the lens or elliptical biopsy 313 contains the hair bulge 317 and bulb 319. In certain embodiments, the lens or elliptical biopsy 313 produces minimal tissue loss at the epidermis 315 while extracting more tissue in the dermis and upper subcutaneous tissue to preserve the hair shaft 323 with the hair bulge 317 and bulb 319 intact. In certain embodiments, minimal scarring is induced and the hair does not need to be dissected from subcutaneous tissue.

Referring to FIG. 3C, a desired angle of entry is accomplished by using a base 327 for the biopsy device 311. In certain embodiments, the base 327 is relatively flat in comparison to its diameter. In FIG. 3C, the base 327 is round, but may be various shapes in other embodiments. The base 327 may have a size similar to the cross-sectional size of the biopsy device 311. One or more openings 329 may be surrounded on one or more sides by a border 331. The border 331 may have a height above a top surface of the base 327. In one implementation, for example, the height is approximately 0.1 mm, or another suitable height. The one or more openings 329 may be curved and may have a width similar to a width of the cutting member 325 at the widest point of the cutting member 325. An angle of penetration of the cutting member 325 may be varied according to relative locations and angles of the border 331 and the one or more openings 329. The one or more openings 329 may guide the cutting member 325 into tissue. In certain embodiments, the one or more openings 329 fit the cutting member 325 with a relatively narrow tolerance to preserve the desired angle of entry. In certain embodiments, the base 327 is made of plastic and is transparent. In certain embodiments, the base 327 may also be attached to the biopsy device if the one or more openings 329 are narrow enough to accommodate the cutting member 325 in a narrow tolerance.

In one implementation, a scoop-shaped blade biopsy device 111 cuts both vertically and horizontally. In this embodiment, tweezers and/or scissors are not required to stabilize and cut a tissue sample prepared by the biopsy device. In one embodiment, the scoop-shaped blade biopsy device is disposable after use.

Figure 4:
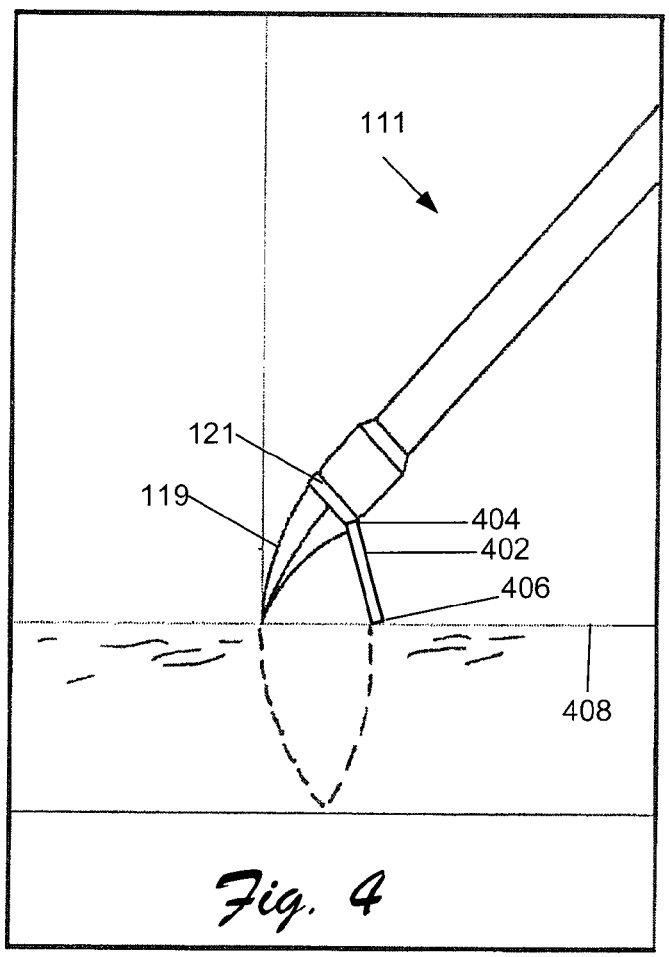
FIG. 4 shows an exemplary scoop-shaped blade biopsy device with an angulator for precise angling of the punch onto skin to perform a biopsy, according to one embodiment.

FIG. 4 shows an exemplary scoop-shaped blade biopsy device with an angulator for precise positioning and angling of the punch to perform a biopsy, according to one embodiment. In this description, a component reference number begins with the figure number where the component was first introduced. Referring to FIG. 4, the scoop-shaped blade biopsy device 111 comprises an angulator 402, which is operatively coupled at portion 404 to the device 111. In one implementation, the angulator is substantially straight and comprised of metal or plastic. In this implementation, the angulator is coupled to connector 121 at the opposite side of blade 119. As shown, angulator 402 has a free end 406 for contact with the surface of a patient's skin 408. The configuration of the connection/coupling 404 allows the angulator to rotate about a fixed position (404) when subjected to a threshold amount of force in relation to the punch's vertical access at the fixed end 404. The threshold amount of force is configurable as a function of the particular implementation of the angulator's connection/coupling to device 111. In one implementation, the coupling/attachment of the angulator to the device 111 is such that a configurable amount of rebound capable of bending in the angulator 402 occurs during use of the device 111 comprising the angulator 402. In one embodiment, angulator 402 is already curved or bent at a point of coupling or thereafter. There are many known techniques that can be used to attach angulator 402 for rotation during use of punch device 111 to extract a biopsy from a patient. In preparation for a biopsy procedure, the offset position of the distal end 406 from the point of blade 119 provides a practitioner with a visual cue/estimation of the extent and size of the biopsy sample that will result from a corresponding biopsy procedure.

Figure 5:
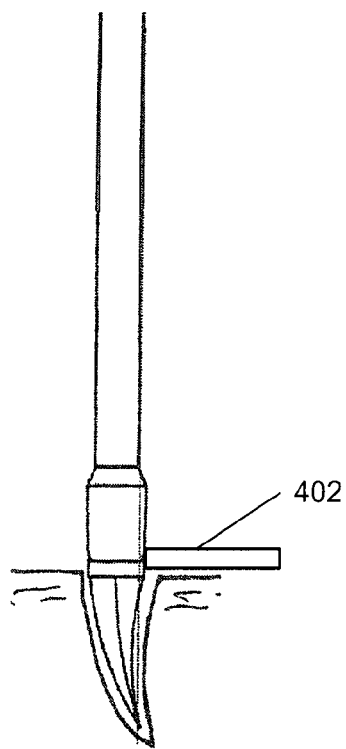
FIG. 5 shows an exemplary scoop-shaped blade biopsy device with an angulator in a substantially horizontal position, according to one embodiment.

In one exemplary implementation, as a practitioner advances the punch blade 119 into a patient's skin 408, angulator 402 is lifted away from the skin; then as the punch goes deeper into the skin, the angulator touches the skin again and is forced outward rotating around its attachment at the connector until it lies horizontal to the skin when blade 119 has been positioned/inserted to a substantially full extent in the patient's flesh. An exemplary view of such horizontal positioning of the angulator is shown in FIG. 5. Once the blade 119 has been positioned to a substantially full extent in the patient's flesh, the biopsy procedure continues as described in preceding sections of this detailed description.

Open Punch Biopsy Device with Tissue Stabilizer

FIGS. 6A through 6E show respective aspects of an exemplary tissue biopsy device 600 with a tissue stabilizer, according to one embodiment. Referring to FIG. 6A, and in this one particular implementation, the device 600 has a circular body 602; a coring blade 604 rigidly connected via connector arm 606 to body 602; a stabilizer arc 608 connected via a rigid actuating arm 610 that terminates in an actuating lever or key 612; the actuating arm 610 being positioned within body 602 and pivotably secured to the body via at least one pivot seat 614, the pivot seat(s) being proximal to the base of the body 602; and an L-shaped key gap 616 comprising a first vertical portion and a second horizontal key locking portion in body 602 through which actuating key 612 extends for the end user to respectively rotate, slide, and/or pivot stabilizer arc 608 during a biopsy procedure. (Various configurations mechanisms for pivot seats are known.) For instance, and as described in greater detail below, stabilizer arc 608 can be moved, or offset, from a neutral tissue biopsy position and directed towards the inner side of cutting blade 604 to constrict the base of tissue during a biopsy operation. In one implementation, the stabilizer arc/portion 608 is not sharp, but rather blunt, and does not participate in cutting of the tissue sample, but merely stabilizing the tissue sample for cutting (e.g., via the cutting blade 604, other cutting means, etc.).

FIG. 6B shows an exemplary implementation of a key gap 616 in the biopsy device 600 to allow for movement of the stabilizer arc 608 via actuating key 612, according to one embodiment. Horizontal and vertical extents of key gap 616 are configurable allowing for specified amounts of inward and outward movement of stabilizer arc 608. In FIG. 6B, actuating key 612 is in a vertical portion of a key retaining gap 616 in the biopsy device.

FIG. 6C shows an exemplary spring 618 (e.g., an exemplary compression component) operatively attached to an inner wall 620 of body 602, according to one embodiment. In this example, actuating key 612 is in contact and compressing spring 618. Please note that spring 618 is configured to compress and store tension responsive to a practitioner pressing down on the key 612, for example, from a first position, e.g., where the key is positioned near the top of the vertical portion of gap 616 (e.g., FIG. 6B), to a second position downwards and towards the horizontal portion of gap 616 (e.g., as shown in FIG. 6D). Techniques to operatively couple a spring to a device such that the spring will compress and retract responsive to specified stimulus are well known. In this implementation, the at least one spring 618 is shown as being disposed at an acute angle to body 602. However, other spring types and configurations can also be used to provide the described key snap-back and controlled movements of the stabilizer arc 608. In one implementation, spring 618 is an elastic component that recovers its shape after being compressed, bent, or stretched.

FIG. 6D shows an exemplary configuration of actuating key 612 in a locked position in key gap 616, according to one embodiment. In the illustrated key position orientation, spring 618 (FIG. 6C) remains compressed without manual assistance when key 612 is in the locked position in gap 616. Responsive to a practitioner moving key 612 out of the stabilizer locked position (i.e., where the key 612 is positioned anywhere in the horizontal portion of gap 616), spring 618 will release its tension (compressed/stored energy), causing stabilizer arc 608 to snap back to a neutral position. Such a neutral position is characterized, for example, by: (a) the actuating arm being substantially parallel to the fixed connector arm 606; (b) the spring being in a substantially uncompressed state; and (c) stabilizer arc 608 being positioned with respect to cutting blade 604, for example, as shown in FIG. 6E. FIG. 6E is an exemplary illustration showing the position of the gaps between cutting blade 604 and stabilizer arc 608 according to one embodiment, and as viewed looking down on the distal ends 620 and 624 (FIG. 6A).

Referring to FIG. 6A, the length of the stabilizer arm 610 is configurable. For example, in one implementation, the lower end 620 of the stabilizer arc 608 is at least one quarter (¼) of the punch's depth (or ¼ length of the exposed arm 606 coupled to cutting blade 604). This exemplary configuration ensures that the stabilizer arc 608 may still constrict/grasp the tissue when actuated (such actuation is described below). In one implementation, handle 602 is longer or shorter than shown, and arm gap 615 extends downwards to the distal end of the longer or shorter handle to allow movement of stabilizer arm 610 from pivot point 614. The material thickness of body, connector arm 606, core blade 604, actuating arm 610, and stabilizer 608 are selectively configurable such that the components can withstand and efficiently perform the biopsy procedure (e.g., a sharp set of edges on the core and stabilizers). In one implementation, the tissue coring portion of the biopsy device is made from one or more types of sturdy medical grade materials, such materials being suitable for sterilization and/or disposal after each use. The medical grade materials do not chemically leach when in contact with tissue samples. In one implementation, for example, such medical grade materials include stainless steel. In one implementation, the distal edge 622 of the stabilizer arc 608 is not sharp, and the size of its arc is smaller than the gap that lies in the punch wall.

An exemplary procedure to use blade biopsy device 600 to take a patient (human or animal) biopsy is now described. A practitioner starts the biopsy procedure by placing the distal edges 622 and 624 of the cutting blade 604 and stabilizer arc 608 perpendicular to, and disposed over and in contact with, a desired tissue portion of the patient's skin. The practitioner then pushes and twists/rotates the handle 602 of the device to penetrate and cut deep into the patient's tissue until the desired biopsy core depth is achieved. At this point, the practitioner cuts the base of the tissue core by select ones of several possible techniques, as now described. In one exemplary biopsy process, "A," the practitioner manipulates actuating switch/lever 612 downwards into the locking position short arm of L-shaped gap 616 to pivot and move stabilizer 608 towards core blade 604. This substantially horizontal/planar movement of the stabilizer 608 constricts and traps the patient's tissue sample (i.e., the tissue subject to the biopsy operation) at its base by pushing the tissue closer to cutting core blade 604, effectively narrowing the diameter of the cutting portion defined by blades 604 and 608. While the planar movement of the stabilizer is substantially horizontal, the movement may have a relatively small vertical component caused at least by the described pivoting mechanism for moving the stabilizer inward to cut the base of a cored tissue sample.

In this example "A," and after the practitioner actuates lever 612 into the horizontal portion of gap 616 to trap and cut the tissue sample at its base, the practitioner pulls/extracts the device 600 from the patient while moving/rotating the device back and forth and pivoting/bending relative to an axis perpendicular to the base plane of the tissue sample. In one embodiment, such an axis is defined by the practitioner's grasp of the device body 602. Accordingly, the base of the tissue sample is cut by respective ones of blades 604 and 608, and the resulting biopsy is released from the patient. When the tissue has been retrieved from the patient, the tissue is extracted from the stabilizer biopsy device 600 by releasing the key back to its neutral position, causing the spring 618 to release its tension, snapping the stabilizer arc and actuating arm, including the key back to their neutral positions.

D1 Protrusion

Figure 7A:
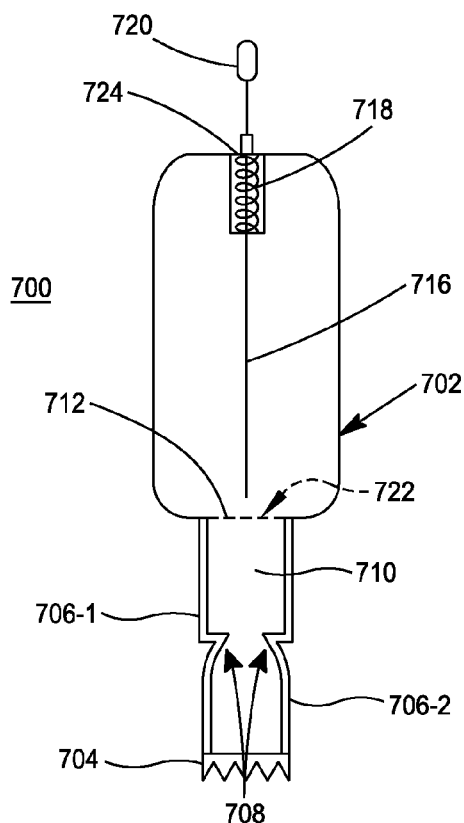
FIG. 7A shows an exemplary tissue biopsy device 700 with cored tissue retaining protrusions or indentations, according to one embodiment.

FIG. 7A shows an exemplary tissue biopsy device 700 with cored tissue retaining protrusions or indentations, according to one embodiment. In this embodiment, the tissue biopsy device includes a handle end 702 and a hollow circular cutting end 704 joined together by two arms extending at either side 706-1 and 706-2. As such, this is an open punch design that facilitates release of a tissue specimen from the tissue retaining portion of the punch. The tissue retaining portion of the punch comprises that open area between the arms 706 and the cutting end 704. In this implementation, the cutting end is serrated. In another implementation, the cutting portion is not serrated.

As shown in FIG. 7A, the tissue retaining portion includes narrowing protrusions or intrusions, shown by indentations 708 (side view). In one implementation, and when the punch biopsy device is viewed from the outside or exterior, the narrowing portions may appear as respective intrusions, for example, when rigid connecting arms are bent towards the interior of the punch's tissue retaining portion, as described below. When viewed from the interior of the tissue retaining portion of the biopsy device, the narrowing portions will appear as protrusions from the walls of the rigid connecting arms. Although respective positions of these indentations 708 are individually configurable, in this implementation, the indentations 708 are positioned directly across from one another and substantially in the middle of the arms 706 (i.e., 706-1 and 706-2). Indentation(s) 708 are configured with a gentle slope on their proximal side (the side closest to the cutting end 704) and a substantially planar orientation that is perpendicular to the long axis of the device 700 on the distal side (the side closest to the handle 702). As such, when the cutting edge 704 of the tissue biopsy device 700 is pushed down into a patient's tissue to obtain a tissue sample, the indentation(s) 708 will constrict, but not substantially impede or stop, the tissue from advancing past the indentations and into the upper portions 710 of the tissue retaining portion. As such, the structural design/configuration of the indentations 708 allow the advancing tissue to pass by the narrower area to occupy the upper circumference area 712 of the tissue retaining portion. As a practitioner pulls the tissue biopsy device 700 out of the patient to remove the cored sample (see core 728 of FIGS. 7B and 7C), the constraining design of indentations 708 hold the sample within the retaining portion 706, while the practitioner twists and angles the device 700 to bring the base of the tissue closer to the cutting blade 704 to slice the base of the tissue sample with cutting edge 704 (or other cutting instrument).

In one implementation, the indentations 708 are bent portions of the arms 706. In another implementation, the indentations are the result of a molded arm 706 that curves in and back. In another implementation, the arms 706 are straight, and the indentations are formed on the inner arm walls with additional material.

Figure 7B:
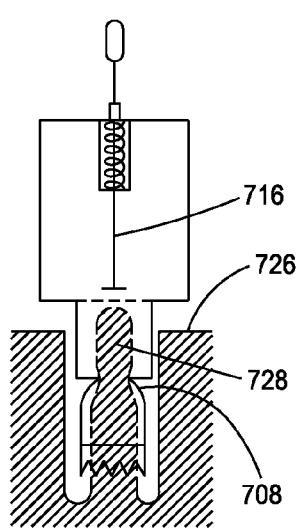
FIG. 7B shows an exemplary use of the punch biopsy device to create a tissue core in a patient's flesh, according to one embodiment.
Figure 7C:
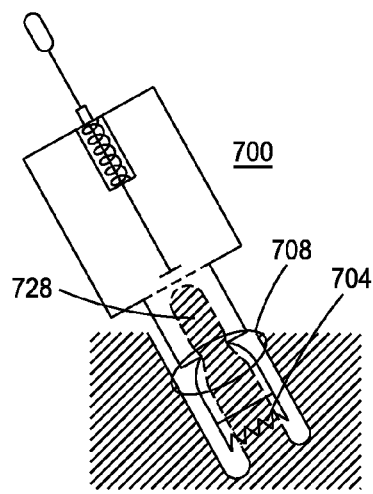
FIG. 7C shows an exemplary angling of the punch biopsy device, which will typically occur when a practitioner begins to position the cutting end to cut the base of the tissue sample.

FIG. 7B shows an exemplary use of the biopsy device to create tissue core 728 in a patient's flesh 726. Please note that in this example, the base of the tissue core has not been cut. FIG. 7C shows an exemplary angling of the biopsy device 700, which will typically occur when a practitioner positions the cutting end 704 to begin to cut the base of the tissue sample.

Referring to FIG. 7A, in one implementation, tissue biopsy device 700 may include a set of tissue removing components comprising a displacer 716 (a displacement arm or rod) passing through a retaining channel 718 extending, for example, from the distal end of the handle 702. To use the tissue removing component, and after the base of a cored tissue sample has been cut, a practitioner presses down on displacer end 720 (e.g., with a thumb or finger) to move the displacer 716 down past boundary 722 and towards cutting edge 704. This movement causes the remote end of arm 716 to make contact with and press downwards on the top of a tissue sample in the tissue retaining portion, thereby pushing a cored tissue sample past indentation(s) 708 and out of the tissue retaining area. Tissue generally shrinks when taken outside the body, because of drying and loss of blood. Therefore, dispensing the tissue by the displacer will be met by less resistance by indentation(s) 708 when it dries up in the air. In one implementation, channel 718 includes spring 724 (FIG. 7*a*) operatively coupled to the arm 716 and biopsy device handle 702. The spring is configured to return the arm 716 to a neutral position after the spring has been compressed by a practitioner during tissue sample removal operations, or otherwise.

S1 Cutter Biopsy Device

Figure 8:
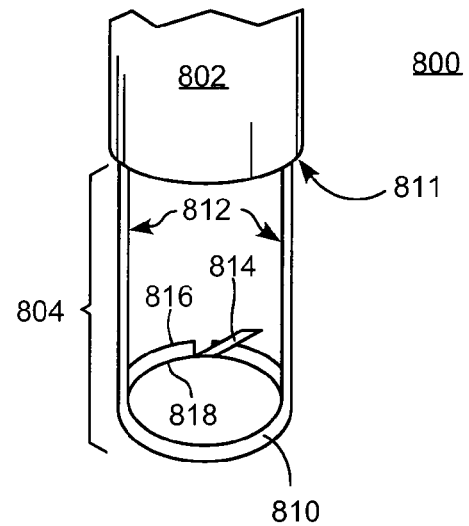
FIG. 8 shows an exemplary tissue biopsy device with a cutting blade that comprises a sharp-edged prong for cutting the base of the tissue sample, according to one embodiment.
Figure 9:
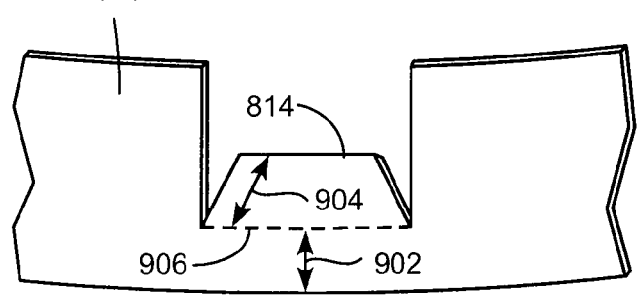
FIG. 9 shows an exemplary prong retaining portion at the distal end of the prong 814, wherein the prong retaining portion is integral with the cutting blade, according to one embodiment.

FIG. 8 shows an exemplary tissue biopsy device, according to one embodiment. As shown, the biopsy device 800 comprises two components, a handle 802 and a cutting/coring portion 804, operatively coupled to one another at portion 811. In one implementation, the cutting portion is made from surgical grade stainless steel. The cutting portion comprises first and second rigid arms 812 that terminate in a circular cutting blade 810. The vertical edges of arms 812, the boundary portions of handle 802, and the proximal/top edge of the cutting blade 810 bound empty space (i.e., a wall defined by these boundaries are missing/void). Circular blade 810 is operatively coupled to handle 802 by two rigid arms 812. Circular cutting blade 810 comprises a prong 814 with sharp top and lateral edges. The prong is flexibly and rotatably coupled or integral to a portion of the cutting blade 810. In one embodiment, prong 814 is formed via two cuts in the cutting blade (i.e., the prong is formed from material of the cutting blade and delimited/bounded via two cuts in the blade), wherein each cut begins at a proximal/top edge 816 of the cutting blade, trending towards a distal edge 818 without meeting or severing through the distal edge 818. In another implementation, the cuts can begin from the bottom and trend towards the top of the cutting blade. Either implementation provides for a base of the prong that trends into the structure of the cutting blade 810—also referred to as a prong retaining portion 902, as shown in FIG. 9. In this implementation, the material of the cutting blade is relatively flexible, allowing the prong 814 to be rotatably positioned towards the center (inwards) of cutting blade 810 and back to a neutral position that is parallel with the longer axis of the walls in the cutting blade.

Prong 814 has three (3) razor sharp edges except for its distal end that is flexibly or rotatably attached and/or integral to/with the cutting blade 810. As a practitioner pushes biopsy device 800 into the flesh of a patient, cutting blade 810 cuts the tissue in the direction of the insertion. During this device insertion stage, the prong, by virtue of its shape and rotatable/flexible attachment to the cutting blade, rotates toward the handle 802 from a 45 degree angle (in this example) to allow the cored tissue to advance into tissue retaining portion 804. To this end, the prong 814 folds towards the handle until it is substantially parallel to the longer axis of the walls of the cutting blade 810, in the instance where a tissue core at least as long as the length of the prong is taken. However, as the cutting portion 804 of the biopsy device is pulled out of the patient, the sharp end of the prong 814 catches the passing cored tissue, e.g., responsive to (or independent of) the practitioner's angling or twisting of the biopsy device. This "catching" causes the prong to rotate about its axis (see axis 906 of FIG. 9) inward and toward the center of the core retaining portion 804. In this scenario, as the device 800 is extracted from a patient during a coring procedure, the prong resists, eventually catching/snagging and piercing the cored tissue as the prong rotates from a position substantially parallel to the wall of cutting blade 810 to a position that is substantially perpendicular to the walls of the cutting blade. When the prong has reached a position that for example, is substantially perpendicular to the walls of the cutting blade, the practitioner rotates the device 360 degrees around its vertical axis to sever the base of the cored tissue sample.

FIG. 9 shows an exemplary prong retaining portion 902 at the distal end of the prong 814, wherein the prong retaining portion is integral with cutting blade 810, according to one embodiment. In this exemplary illustration, prong 814 is bent towards the inner portion of the circular cutting blade 810 and positioned at approximately 45% from normal horizontal, although it can also be flexed so that it is substantially parallel to the walls of the cutting blade 810. In this implementation, prong 814 has a vertical dimension 904 that allows the prong 814, when rotated substantially perpendicular to the longer axis of cutting blade 810, to extend substantially to or past the center of the circular cutting blade 810, wherein the center is a radius length of circular cutting blade 810. This will ensure that the prong reaches/cuts at least to the center of the tissue as the biopsy device 800 (FIG. 8) is rotated to cut the base of the cored tissue. In one implementation, more than one prong 814 is utilized in the cutting blade 810 to aid in the dissection of cored tissue.

FIGS. 10A-10C show various aspects of an exemplary biopsy device with a base cutting prong being used to take a tissue core, according to one embodiment. An exemplary procedure to use device 800 to obtain a tissue biopsy from a patient starts with vertical cutting, without substantial twisting, until a desired depth is reached as shown in FIG. 10A. Please note that at this state, prong 814 is substantially parallel to the long axis of the cored tissue or the long axis of the biopsy device. At this stage, the practitioner lifts the cored tissue/skin plug 1002 by lifting the biopsy device out of the patient. As the tissue is pulled/lifted, the end of the prong 814 catches the tissue and penetrates deeper into the cored tissue, flexing down and piercing the cored tissue. Continued lifting up of the biopsy device will eventually cause the prong to be substantially horizontal, as shown in FIGS. 10B and 10C. At this point, and in one implementation, prong 814 is restricted from rotating or bending/flexing anymore because the point at which the cutter is connected to the cutting member restricts further rotation; and tissue overlying the cutter at a substantially 90° angle prevents the cutter from moving back into neutral position—i.e., parallel with the long axis of the device 800. The surgeon then rotates the punch 800 and severs the base of the cored tissue, as shown in FIG. 10C. The severed specimen 1004 then can be lifted up inside the punch for removal and stored in a container.

Closed Punch Biopsy Device with Automatic Tissue Dispenser

Figure 11:
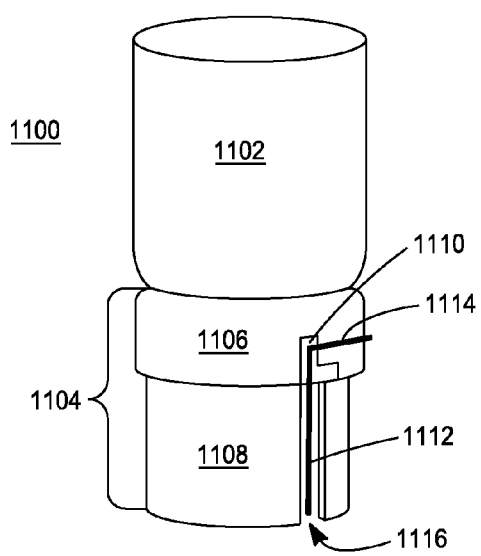
FIG. 11 shows exemplary aspects of a punch biopsy device comprising a tissue sample stabilizing arm assembly, according to one embodiment.

FIGS. 11 through 14 show respective aspects of an exemplary tissue punch biopsy device comprising a tissue sample stabilizing arm assembly, according to one embodiment. Referring to FIG. 11, there is shown a punch biopsy device 1100 comprising a handle 1102. The handle is for grasping by a practitioner to take a tissue biopsy. In this particular illustration, and in FIG. 12, the handle is only partially illustrated, as numerous different handle configurations for punch biopsy devices are known. Handle 1102 is operatively coupled to a tissue coring portion 1104 that comprises a body 1106 and a circular coring blade 1108. The body comprises a stabilizer bar actuating key gap 1110, similar to that described above in reference to FIGS. 6A-6D. Punch biopsy device 1100 further comprises a stabilizer arm 1112 that is configured at its proximal end with an actuating lever/key 1114. The stabilizer arm 1112 and actuating lever 1114 assembly are pivotably coupled to the body 1106 via a pivot seat mechanism such as that used in the punch biopsy device 600 described above in reference to FIG. 6A. Additionally, a spring assembly is operatively coupled to the inner portion of body 1106 such that when a practitioner moves the actuating arm 1112 downwards in the vertical portion of key gap 1110, the spring compresses. The spring remains compressed while the actuating lever has been positioned in the horizontal lower portion of the key gap 1110. Responsive to a practitioner releasing the actuating arm in the lower vertical portion of the key gap, the compressed spring releases its stored energy and snaps the stabilizer arm back to a substantially neutral position that does not substantially constrict any tissue within the device retaining portion 1104. Such a neutral position, shown in FIG. 11, is substantially parallel to the walls of the cutting blade 1108. An exemplary spring configuration for punch biopsy device 1100 is described above and shown with respect to punch biopsy device 600 described above in reference to FIGS. 6A-6C.

Figure 12:
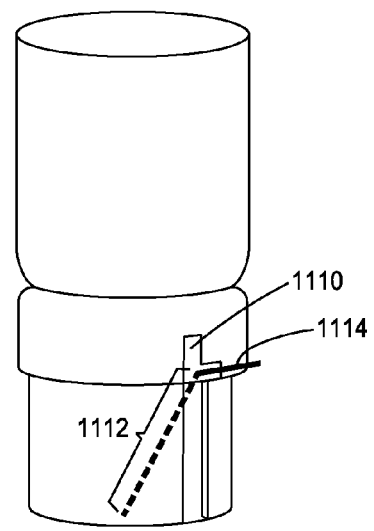
FIG. 12 shows an exemplary punch biopsy device with a stabilizer arm in a position to contact and stabilize any cored tissue within the tissue retaining portion, according to one embodiment.

FIG. 12 shows an exemplary punch biopsy device 1100 with a stabilizer arm 1112 in a position to contact and stabilize any cored tissue within the tissue retaining portion 1104, according to one embodiment. As shown, the actuating lever 1114 is positioned in the horizontal/locked portion of the L-shaped key 1110. Although stabilizer arm 1114 of punch biopsy device 1100 does not terminate in a stabilizer arc 608, as described above in reference to the punch biopsy device 600 of FIG. 6A, the stabilizer arm 1114 is utilized to constrict cored tissue within the tissue retaining portion of the punch biopsy device in a substantially similar manner in this particular implementation. For example, a practitioner utilizes the stabilizer arm and its actuating lever to stabilize a cored tissue within the retaining portion of the punch biopsy device. During tissue stabilization operations, the practitioner can cut the base of the cored tissue, for example, by twisting, rotating, and angling the sharp distal end of the cutting blade 1108 such that the sharp edges of the cutting blade sever the base of the cored tissue, as described above with respect to various biopsy device embodiments. Alternatively, the practitioner can utilize the stabilizer arm to hold the tissue in place while lifting the biopsy device out of the patient to expose an elongated base portion of the cored tissue still attached to the patient, whereupon a scalpel, scissors, or other cutting device can be used to sever the base of the cored tissue. In this particular implementation, and to allow a practitioner to remove a cored tissue biopsy having a severed base from the tissue retaining portion 1104 of the biopsy device 1100, cutting blade 1108 comprises a gap 1114 large enough for the practitioner to gain access to and press the cored tissue out of the tissue retaining portion 1104. Devices and techniques to press cored tissue out of a gap in a punched biopsy device are known.

Figure 13:
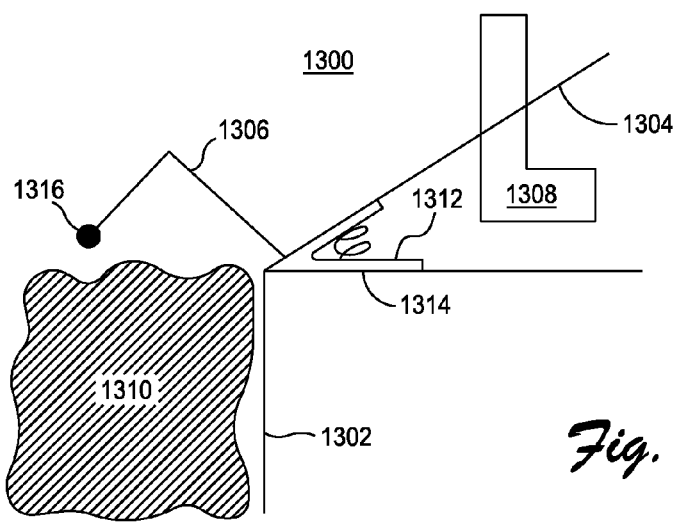
FIG. 13 shows an exemplary stabilizer/displacer assembly, according to one embodiment.

FIG. 13 shows an exemplary stabilizer/displacer assembly 1300, according to one embodiment. In this implementation, the stabilizer/displacer assembly includes a stabilizer arm 1302 that terminates in an actuating lever 1304, wherein the stabilizer arm is operatively coupled to or an integral part of a displacer arm 1306. In one implementation, the stabilizer/displacer assembly 1300 replaces the stabilizer arm 1112 actuating lever 1114 assembly in the punch biopsy device 1102 of FIGS. 11 and 12. In such an implementation, the stabilizer bars 1112 and 1302 and the actuating lever's 1114 and 1304 have essentially the same function and operation as described with respect to FIGS. 11 and 12. For instance, the actuating assembly 1304 is presented and utilized by a practitioner via an actuating arm key gap 1308, which in this particular implementation is L-shaped. The practitioner would utilize the actuating arm to constrict a cored tissue sample 1310 within a tissue retaining portion (e.g., 1104 of FIG. 11) with the stabilizer arm 1302. As the stabilizer arm/bar is moved downward and at the key gap 1308, a spring 1312 operatively attached to an inner wall (e.g., via an indentation or ridge 1314 on the interior of the wall) of the punch biopsy device compresses, storing its energy within the spring. However, in contrast to the stabilizer/actuating assembly described above with respect to FIGS. 11 and 12, when the practitioner releases the actuating arm 1304 out of the horizontal locked position in gap 1308, the rapid release of energy in the spring 1312 causes not only the actuating lever 1304 to move upwards in the vertical portion of the gap 1308, but also causes the displacer arm 1306 to move inside of the punch. Specifically, the displacer arm 1306 moves towards the top of the tissue sample 1310 until forceful contact with the upper portion of the tissue sample 1310 is realized. Such forceful contact automatically removes the lodged tissue sample 1310 from the tissue retaining portion of the punch biopsy device, for example, into a container. In this scenario, the stabilizer arm 1302 has an extended range of movement and is allowed to move outside of the cutting blade circumference, for example, through a gap in the cutting blade such as gap 1116 of FIG. 11.

In one implementation, the displacer arm 1306 terminates in a blunt end 1316 designed to not pierce the contacted portion of the tissue sample. Although the blunt end 1316 of FIG. 13 is shown as a circular portion, such a blunt terminal portion of the displacer arm 1306 could be a different shape, for example, a planar shape. In one implementation, if release of the tension in the spring is not sufficient to automatically remove the tissue sample from the tissue retaining portion of the punch biopsy device, the displacer/displacement arm 1306 will facilitate removal of the tissue sample from the tissue retaining portion.

Figure 14:
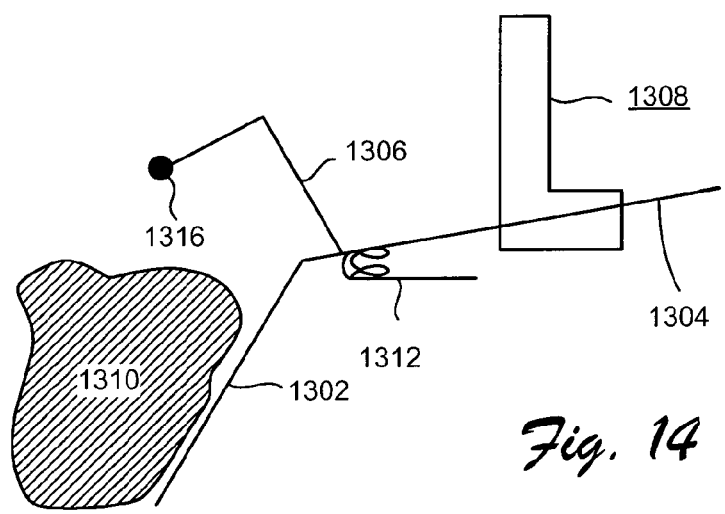
FIG. 14 shows the displacer assembly of FIG. 13, wherein the actuating arm is in a locking position in the key gap, and wherein the stabilizer is stabilizing tissue in the tissue retaining portion of a punch biopsy device.

FIG. 14 shows the displacer assembly of FIG. 13, wherein the actuating arm is in a locking position in the key gap, and wherein the stabilizer is stabilizing tissue in the tissue retaining portion of a punch biopsy device.

Conclusion

Although systems and methods for a biopsy device have been described above in language specific to structural features and/or methodological operations or actions, the implementations defined in the appended claims are not necessarily limited to the specific features or actions described. Rather, the specific features and operations for the stabilizer biopsy device are disclosed as exemplary forms of implementing the claimed subject matter.

The invention claimed is:

1. A punch biopsy device comprising:
   a cutting blade with first and second arms operatively coupled to a handle, and the cutting blade being circular in shape; and
   a prong flexible and integral to the cutting blade, the prong comprising a top sharp edge and lateral sharp edges configured to pierce and cut tissue, respectively, each of the lateral sharp edges extending from the cutting blade to the top sharp edge of the prong;
   wherein the prong is configured to be inserted into a body in a neutral position with the prong parallel with the first and second arms;
   wherein the prong is configured to move to a position perpendicular to the first and second arms as the cutting blade is pulled out of a patient to allow for the prong to catch and pierce the tissue; and wherein the prong is configured to cut the tissue along a distance from the cutting blade to the top sharp edge of the prong while in the position perpendicular to the first and second arms when the cutting blade is rotated manually via the handle.

2. The punch biopsy device of claim 1, wherein the prong is defined by two boundary cuts in the cutting blade, wherein each cut of the two cuts extends through a proximal edge of the cutting blade, each cut trending towards a distal edge of the cutting blade without extending through the distal edge of the cutting blade.

3. The punch biopsy device of claim 1, wherein vertical edges of the first and second arms together with a distal boundary of the handle and a proximal edge of the cutting blade define hollow spaces therebetween.

4. The punch biopsy device of claim 1, wherein the length of the prong is at least half of the diameter of the cutting blade and the prong is configured to reach at least a center of the tissue within the cutting blade.

5. The punch biopsy device of claim 1, wherein the length of the prong is at least half of the diameter of the cutting blade, the prong is configured to reach at least a center of the tissue within the cutting blade, and the prong is configured to sever a complete base of the tissue within the cutting blade when the cutting blade is rotated 360 degrees around a vertical axis extending between the first and second arms and within the cutting blade.

* * * * *